(12) United States Patent
Lupinetti et al.

(10) Patent No.: US 7,528,343 B2
(45) Date of Patent: May 5, 2009

(54) LASER TREATMENT OF SANITARY PRODUCTS

(75) Inventors: Serafino Lupinetti, Elice (Pescara) (IT); Paolo Pasqualoni, Sambuceto di San Giovanni Teatino (Chieti) (IT)

(73) Assignee: Fameccanica. Data S.p.A., Sambuceto di San Giovanni Teatino (Chieti) (IT)

( * ) Notice: Subject to any disclaimer, the term of this patent is extended or adjusted under 35 U.S.C. 154(b) by 440 days.

(21) Appl. No.: 11/391,955

(22) Filed: Mar. 29, 2006

(65) Prior Publication Data

US 2006/0283846 A1 Dec. 21, 2006

(30) Foreign Application Priority Data

Jun. 21, 2005 (EP) .................................. 05425450

(51) Int. Cl.
*B23K 26/38* (2006.01)

(52) U.S. Cl. ........................... 219/121.72; 219/121.67; 219/121.81

(58) Field of Classification Search ............ 219/121.71, 219/121.74, 121.8, 121.82, 121.67, 121.72
See application file for complete search history.

(56) References Cited

U.S. PATENT DOCUMENTS

| 4,623,229 | A | * | 11/1986 | Galan | 219/121.63 |
| 5,200,592 | A | | 4/1993 | Yabu | 219/121.67 |
| 5,262,612 | A | | 11/1993 | Momany et al. | 219/121.67 |
| 5,357,365 | A | | 10/1994 | Ipposhi et al. | 359/205 |
| 5,792,301 | A | * | 8/1998 | Calvert et al. | 156/272.8 |
| 5,886,319 | A | | 3/1999 | Preston et al. | 219/121.72 |
| 6,177,648 | B1 | | 1/2001 | Lawson et al. | 219/121.62 |
| 6,191,382 | B1 | | 2/2001 | Damikolas | 219/121.62 |
| 6,252,196 | B1 | * | 6/2001 | Costin et al. | 219/121.69 |
| 6,327,875 | B1 | | 12/2001 | Allaire et al. | 65/103 |
| 6,388,231 | B1 | * | 5/2002 | Andrews | 219/121.69 |
| 6,433,301 | B1 | | 8/2002 | Dunsky et al. | 219/121.67 |
| 6,501,047 | B1 | * | 12/2002 | Xuan et al. | 219/121.69 |
| 6,697,408 | B2 | * | 2/2004 | Kennedy et al. | 372/55 |
| 2002/0003129 | A1 | * | 1/2002 | Mukasa et al. | 219/121.63 |
| 2002/0130462 | A1 | * | 9/2002 | Dobrindt | 271/272 |
| 2003/0006217 | A1 | | 1/2003 | Dance | 219/121.18 |
| 2003/0212377 | A1 | * | 11/2003 | Karlsson et al. | 604/387 |

(Continued)

FOREIGN PATENT DOCUMENTS

DE 196 05 888 A1 8/1997

(Continued)

OTHER PUBLICATIONS

European Search Report for Application No. EP 05 42 5450, dated Feb. 21, 2006, 9 pages.

*Primary Examiner*—Geoffrey S Evans
(74) *Attorney, Agent, or Firm*—Victor A. Cardona, Esq.; Heslin Rothenberg Farley & Mesiti P.C.

(57) ABSTRACT

A device for subjecting to laser treatment articles, in particular articles chosen between sanitary products and components of said products, comprises a laser-beam source configured for applying to the articles a laser spot with a diameter of between 50 μm and 2000 μm. Preferentially, the laser spot has a wavelength of between 9.0 μm and 11.0 μm The control unit is configured to regulate jointly the power of the laser spot, the instantaneous relative speed of the laser spot with respect to the article treated, and the instantaneous diameter of the treatment laser spot.

38 Claims, 3 Drawing Sheets

U.S. PATENT DOCUMENTS

| | | | |
|---|---|---|---|
| 2004/0045323 A1 | 3/2004 | Schultz et al. | 65/392 |
| 2004/0211763 A1* | 10/2004 | Lambert | 219/121.84 |
| 2005/0049129 A1* | 3/2005 | Belcastro et al. | 493/63 |
| 2005/0098547 A1 | 5/2005 | Cali et al. | 219/121.72 |
| 2005/0155956 A1* | 7/2005 | Hamada et al. | 219/121.69 |

FOREIGN PATENT DOCUMENTS

| | | |
|---|---|---|
| EP | 1 447 068 A1 | 8/2004 |
| EP | 1 447 068 A3 | 8/2004 |
| JP | 61-67926 A * | 4/1986 |
| JP | 4-253584 A * | 9/1992 |
| JP | 7-68394 A * | 3/1995 |
| JP | 9-150282 A * | 6/1997 |
| JP | 11-28588 A * | 2/1999 |
| JP | 2001145659 | 5/2001 |
| JP | 2001-225183 A * | 8/2001 |
| WO | WO 96/19313 | 6/1996 |
| WO | WO-03/022510 A * | 3/2003 |

* cited by examiner

"Q" Mode

"D" Mode

"OO" Mode

LASER TREATMENT OF SANITARY PRODUCTS

CROSS-REFERENCE TO RELATED APPLICATIONS

This application claims priority from European Patent Application No. 05425450.3, filed on Jun. 21, 2005, the entire disclosure of which is incorporated herein by reference.

FIELD OF THE INVENTION

The present invention relates to techniques of laser treatment and in particular to the application of said treatments to sanitary products and to the components (including the raw materials) used for making said products.

The invention can be applied, for example, for providing processes of cutting and/or welding using laser technology, to be applied on production lines of single-serve absorbent products such as, once again by way of example, nappies for babies, products for incontinence, pantie-liners for women, moist and dry wipes of various sorts, and detergents in single-dose packages of any type.

DESCRIPTION OF THE KNOWN ART

Currently, to carry out a welding and/or cutting operation on products such as the ones mentioned previously mechanical units are used, usually referred to as "heads".

Limiting our analysis for reasons of simplicity just to the cutting process (it being understood that what is said in regard to cutting substantially applies also to the process of welding), a cutting head usually comprises a frame, a counter-blade roller and a blade roller, as well as various accessory elements, such as systems for cleaning the counter-blade and the blade, lubrication systems, and a system of application of the cutting force. The unit is motor-driven, ensuring transmission of the movement to the mobile parts thereof.

The blades are made of specific materials. Normally, in order to have a particularly hard and hence wear-resistant cutting edge, either special steels are used, such as for example steels for tools, or else sintered materials consisting of tungsten carbide (HM). The hardnesses that can be obtained with steel and HM are not comparable with one another: in fact, in the former case hardnesses of between 60 and 64 HRC are obtained, whereas, in the latter case, hardnesses of up to 1,600 HV10 are obtained. Of course, also the blade life and costs involved are proportional to the hardnesses.

The current technology of cutting heads suffers from various problems.

In the first place, steel blades have limited duration: in the best of cases (even resorting to particular solutions, special steels, and controlled thermal treatments), they do not have durations higher than 20 million "cuts", where the term "cuts" is used to mean the individual cutting operations.

Blades made of hard metal are of longer duration and can easily reach 100 million cuts, but present the problem of sharpening. Whereas for steel it is easy to find workshops equipped and capable of reworking this type of blades, blades made of hard metal, to be sharpened correctly, call for the intervention of the manufacturer of the blade itself. This need results inevitably in a "bottleneck" in the production process that uses said blades.

Another important limitation of the current technology is that of the change of size (i.e., of the dimensions and/or of the format of the products). In this case, it is necessary to replace the entire head, which implies a considerable waste of time and hence loss of production. Obviously, any modification, even a minimal one, in the shape of the cutting profile entails the purchase of a new blade roller.

A further set of problems of mechanical-cutting technology derives from the limitation on the shape due both to the production process and to the problems linked to the cutting process itself.

In particular, in the first case there are limitations on the radius of radiusing of convergent cutting edges, which cannot be less than 3 mm, whereas in the second case, for example, it is not possible to perform cross cuts, because in this case it is necessary to have very high cutting pressures that damage the entire system, drastically reducing the life of the blades.

To overcome the problems linked to mechanical-cutting technology, the possibility of exploiting the potential linked to laser technology has already been considered for some time now.

In this connection, reference may be made to the Japanese patent application No. P2001-145659, which describes, precisely, a method for making absorbent products using laser equipment for performing a function of cutting along a defined treatment path, for each article, from at least one first branch and one second branch.

In more concrete terms, the document No. EP-A-1 447 068 describes a method for treating, using a laser beam and pre-defined paths, products such as sanitary articles that are moving in a given direction. The treatment involves a relative movement between the articles and the laser beam along a path which, for each article, comprises at least one first branch and one second branch. The method described envisages the presence of at least one first laser beam and one second laser beam for carrying out the treatment. The beams are deflected in a transverse direction and, preferentially, also in a longitudinal direction with respect to the direction of advance of the articles, and each of them defines, for each of the articles, respectively, the first branch and the second branch of the treatment path.

The document No. EP-A-1 447 068 corresponds to a considerable improvement as regards the individual treatment assemblies, also as regards correct distribution of energy along the cutting profile, for the purpose of preventing undesirable effects on the products treated. The document in question describes the choice of using generators capable of treating at least two laser beams, which are able to operate independently, for the purpose of simplifying and improving the required processing performance.

PURPOSES AND SUMMARY OF THE INVENTION

Albeit taking into account the considerable progress represented by the solution described in the document No. EP-A-1 447 068, the need is still felt for enabling intervention in, and even more control over, the process and the parameters that influence the treatment with laser technology of products such as the sanitary products described above.

Specifically, there is felt the need of having available optimal layouts of machines and equipment and specific controls, purposely developed for the processes, raw materials and products corresponding to said field of application.

The purpose of the present invention is to satisfy completely the needs outlined above.

According to the present invention, said purpose is achieved thanks to a method having the characteristics referred to specifically in the ensuing claims.

The invention also relates to the corresponding device. The claims form an integral part of the technical teaching provided herein in relation to the invention.

BRIEF DESCRIPTION OF THE ANNEXED DRAWINGS

The invention will now be described, purely by way of non-limiting example, with reference to the annexed plate of drawings, in which.

DETAILED DESCRIPTION OF EXAMPLES OF EMBODIMENT OF THE INVENTION

Figure 1:
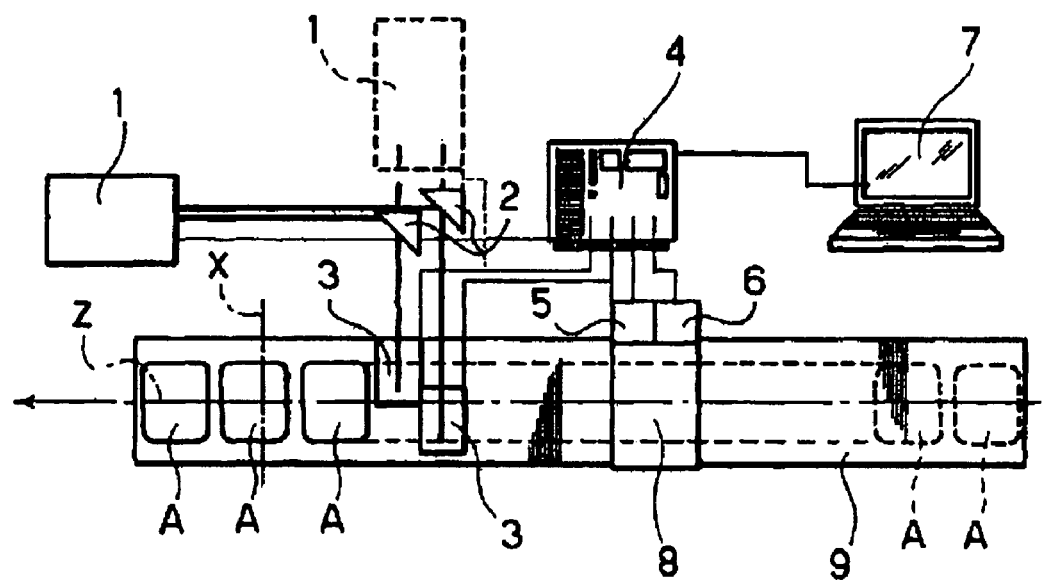
FIG. 1 is a schematic plan view of a device that is able to operate according to the solution described herein.

The diagram of FIG. 1 relates to a general configuration of the device, which as a whole corresponds to the one described in the document No. EP-A-1 447 068 already mentioned previously.

In FIG. 1 the reference number 1 designates a laser-beam source (which may possibly be doubled for reasons illustrated in greater detail in what follows), designed to produce one or more laser beams for the treatment of articles A that are moving (with a speed that will be assumed herein, by way of example, as constant and directed from right to left, as viewed in FIG. 1) in a direction generically designated by z.

The articles A are typically constituted by sanitary products of the type referred to in the introductory part of the present description.

Directed on the articles A, the laser radiation forms on the articles themselves a spot of interaction. Said interaction spot is to exert on the articles A, for example, an action of welding or cutting along a pre-set path, corresponding, for example, to the boundary of the articles A themselves.

Even though the description provided in what follows will not make any further reference to the carrying-out of operations of welding and/or cutting on the articles A, it will be appreciated that the solution described herein can be applied in any context in which it is necessary to subject to laser treatment articles, such as the articles A, or components (raw materials, inserts of various nature, etc.) used for producing the aforesaid articles or products A.

In general, it will be assumed that the treatment can be performed continuously, or else discontinuously, i.e., in discrete points or in stretches, so as to give rise, for example, to spot welding or else to a perforation in discrete points or in stretches (so-called pricking or dinking).

In the example of embodiment illustrated herein (which, it is recalled, is nothing more than an example), the laser beam or laser beams produced by the source 1 (as has already been said, possibly doubled) is sent to two optical transmission units 2 and, from these, to an assembly 3 having a scanning function for controlling the position and collimation of the beam.

In this way, it is possible to direct towards the articles A at least two distinct laser beams, with the faculty of imparting on each beam—independently—a movement of deflection that may be either in the direction of movement of the articles A (axis z of FIG. 1) or in the transverse direction with respect to said direction of movement of the articles A (axis x of FIG. 1).

In a preferred way, the laser source 1 is of the $CO_2$ type, with a total power of 2 kW, with the consequent possibility of having available a power of 1 kW for each beam. The use of a laser source of the aforesaid type is likewise recommended for the wide choice of powers available, which, in the case of needs dictated by the type of raw materials and/or by the high processing speeds (e.g., up to 1000 m/min), enable management of powers of up to 5 kW.

Usually (this aspect is treated more extensively in the sequel of this description) the laser source 1 is equipped for operation with the beam mode of the type OO MODE for the processes of cutting, and with different modes, such as D MODE or Q MODE for the processes of welding.

Using a source or generator 1 capable of emitting two power beams, it is possible to work independently with a beam for each side of the product or article A, it being, however, also possible to operate with just one beam, where required.

For example, supposing that it is necessary to subject to laser treatment (for example, laser cutting of the outline of the product) a nappy-pant (diaper) of a traditional type for newborn babies, i.e., of the type sold "open", it is more convenient and efficient to work with two beams, one for each side.

For a similar product of a pull-on type (of the type sold closed, sometimes referred to also as "training pants") processed in a crosswise direction with respect to the flow Z of the articles A, it is preferable to work with just one beam. In this case, in fact, the shape of cutting of the sheet is a hole having a practically elliptical form centred on the line of transverse cutting that separates two consecutive products. In this case, the laser generator activates the beam as each individual product passes in front of it and, following it, carries out cutting thereof, and then deactivates the beam until the next product arrives.

The scanners for beam collimation and control of position of the laser beam 3 can consist of devices such as, for example, the optical scanning head, model HPM10A, produced by General Scanning Inc. of Watertown (U.S.A.), or else of the products Harryscan 25 or Powerscan 33, manufactured by Scanlab (Germany) or similar products, such as Axialscan or Superscan, manufactured by Raylase (Germany).

In this case, the laser beam leaving the source or sources 1, after passing through the optical transmission units 2, is received by an inlet opening present on each scanner 3 and deviated via a pair of mirrors with fast-recovery galvanometric movement, one for each axis z and x.

Each of the laser beams leaving the scanner 3 is thus able to reach the articles A in the form of a locating spot with dimensions and degree of focusing that could previously be determined. The minimum diameter of the treatment beam (or limit of diffraction of the system) is given by the following relation:

$$d = 1.27 \cdot f \lambda / D$$

where:

d is the minimum section of the spot (limit of diffraction)
1.27 is a constant K of proportionality
f is the focal distance of the lens used
$\lambda$ is the wavelength of the laser beam
D is the diameter of the incoming laser beam on the scanner What is presented above, in its practical application, is to be implemented with another two critical factors described below, which are typical of the quality of the equipment used.

A first factor is represented by the factor of quality ($M^2$) of the laser beam. This is a factor typical of the generator or source used. It describes the deviation of the laser beam with respect to a theoretical Gaussian conformation: in the case of an ideal laser source, a beam that corresponds a theoretical Gaussian, the factor $M^2$ is equal to unity; for real laser beams, $M^2$ is greater than 1.

A second factor is represented by the spherical aberration of the lens. This is a parameter intrinsic to the quality of the lens used, as regards purity of the raw material and precision or type of the processes of surface finishing.

Normally these two factors are included in the constant of proportionality K.

In this connection, it may be noted that the laser generators referred to previously have the possibility of emitting one or more laser beams, having a specific angle of drift, which is a function of the angle of curvature in the output mirrors of the resonator. This involves the formation of a laser beam that is not perfectly parallel.

This pseudo-defect enables the deflection units 3 to be reached with diameter of the beam adapted to that of the incoming light defined by the type of scanner adopted. In other words, in the currently preferred embodiment of the invention, the diameter of the incoming beam and hence of the laser spot applied on the articles A is regulated by varying the optical distance between the source 1 and the scanners 3. This also results in a reduction of the costs of the device as well as in the increase of its efficiency in so far as it is possible to avoid recourse to expansion units and/or lenses for correcting the beam.

To reason in general terms, the range of action of each scanner 3 on the plane of the articles A can be a square or a rectangle that can vary in lateral dimensions within a range typically comprised between approximately 100×100 mm and approximately 500×500 mm, respectively along the axis x and along the axis z, according to the focusing lens used in the scanner 3, which determines the distance from the plane in which the flow of the articles occurs (plane of process) as well as according to the type of scanner adopted (2 axes, 3 axes, etc.).

In the schematic representation of FIG. 1, the reference number 4 designates a H/W electronic control unit (such as, for example, a dedicated computer card), which supervises operation of the system, controlling the action of deflection performed by the scanners 3 on the laser beams, as well as modulation of the power thereof. This occurs according to signals issued by a set of sensors. In the example of embodiment considered herein, said set comprises a sensor 6, which detects the position of the articles A, and a sensor 5, which detects the speed of advance of the articles A along the axis z and the angular position in the creation of the profile reserved to the master unit identified in point 8, with the function, respectively, of master unit (8) and of slave sensor (5). The sensors in question are typically optical sensors, in the case indicated in point 6, of the type, for example, BI2-EG08-APGX-H1341 manufactured by TURK, whereas, in the case indicated in point 5, it is an encoder of an absolute or incremental type, such as Linde AB-6360/2-5 V 1000 ppr or else ROD 420-5000×2 ppr, etc.

The reference number 7 designates in general a processing unit, such as a line controller (Programmable Logic Controller or PLC) or a personal computer (PC) for industrial uses, which supervises operation of the system in which the device represented in FIG. 1 is inserted.

The hardware card 4, like the laser generator 1, are controlled and programmed via a specific software, which can be managed by the unit 7, with the use of control tools and of a graphic interface for the operator (Graphic User Interface or GUI).

Figure 2:
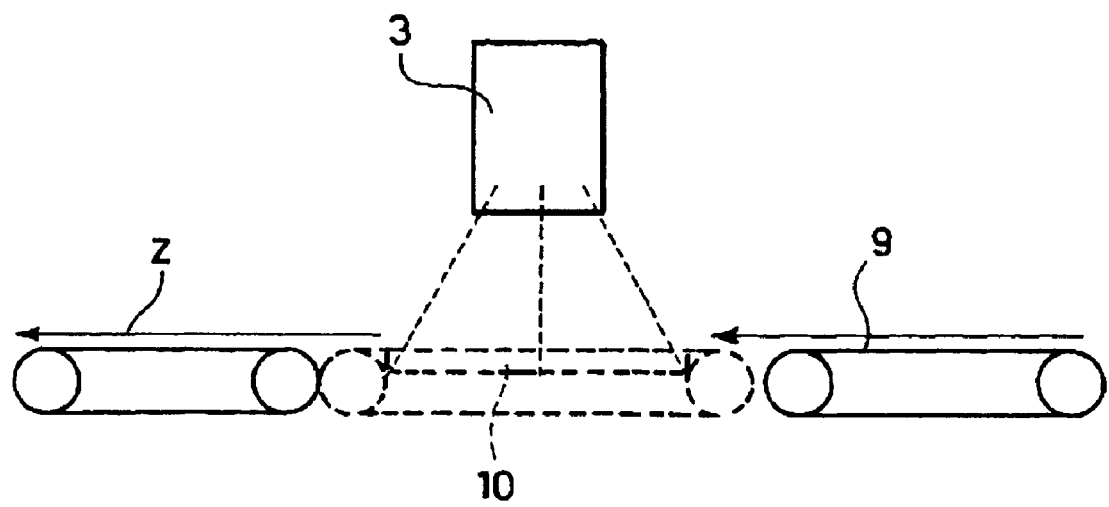
FIG. 2 represents in greater detail, in side elevation, the criteria of operation of the solution described herein.

As may be seen more clearly in FIG. 2, the device also comprises a motor-driven conveying system 9, used to feed the articles A in the direction z. Advantageously, the system in question is formed by a motor-driven belt system comprising for example endless belts, the top branches of which, extending in a generically horizontal direction, function as branches for conveying the articles A.

Of course, the conveying system 9 can be of a type different from what has been illustrated, albeit remaining in the range of solutions well known to the art, which do not need to be described in detail herein.

The same FIG. 2 shows that the scanners 3 are located so as to cause the laser beams to act on the articles A in a well-defined treatment area, designated by 10. In said area there are usually provided devices (not illustrated, but of a known type, for example air-suction devices) for elimination of any possible processing scrap or waste.

In the case where the treatment area is relatively contained along the axis in the direction of the flow z, the support can even be absent in the sense that the article/material treated is simply kept extending in the treatment area, between two consecutive belts.

The support that sustains the articles A during treatment can be fixed or mobile according to the size of the work/treatment window. For example, in the case where, for requirements linked to the process speeds and to the geometry of the article treated, the work window is wide, it is preferable to use a mobile support, such as a conveyor of the type as the one schematically represented in FIG. 2 or a negative-pressure drum, preferentially treated on its surface with the addition of neutral silicone/synthetic material, in thicknesses ranging from 0.5 μm to 5 μm or more, provided that the support so enables. A valid alternative is represented by bristles (either synthetic or not), added in high density on the surface of the support.

In the case of narrow and/or relatively narrow work windows, it is possible to resort to a fixed surface having the same surface characteristics as the ones mentioned previously, or even as was set forth previously, in a vacuum if the jump between the elements for drawing along the flow and the consistency of the raw materials and/or products so permit.

As regards the characteristics of the laser source 1, it emerges that the best treatment results can be obtained, all other parameters being equal, by operating with wavelengths of between 9.6 μm and 11.0 μm, and in a preferred way with a wavelength chosen between 9.6 μm and 10.6 μm. The value 10.2 μm currently represents a particularly preferred value.

Laser sources that correspond to these characteristics of wavelength available on the market are, for example, products sold as CO2 generators by the companies PRC (U.S.A.), ROFIN-SINAR (Germany), Trumpf (Germany), or Laserline (Germany).

Albeit without wishing to be tied down to any specific theory in this connection, the present applicant has reasons to believe that the quality of the results obtained using the values mentioned above is in some way correlated to the characteristics of the materials normally used for producing the sanitary articles in question. Said products identify in fact, together with the corresponding constituent materials, a well-defined type of article to be treated. These are usually white or in any case substantially light-coloured materials, with a translucent or milky appearance, and therefore characterized by a high degree of reflectivity in regard to visible light. In this connection, it should on the other hand be noted that the values of wavelength indicated previously correspond, instead, to radiations lying in the range of the far infrared.

In particular, the source 1 is chosen so as to be able to generate one or more laser beams with the diameter and wavelength mode adapted to the type of treatment being carried out (cutting and/or welding) on the articles A. Said articles are usually moving on the conveying system 9, which, as viewed in FIGS. 1 and 2, acts with the direction of conveyance being from right to left along an axis generically designated by z.

In general, the position and distance of the laser generator 1 in the layout of the device can be parallel or normal to the direction of the flows on the axis z. The choice may depend upon various factors, such as the spaces available, the type of treatment to be carried out, the size of the beam required at input to the deflection unit 3, etc. In addition to what has been said above, it proves economically advantageous to use multi-beam laser sources (possibly with multiple generators), i.e., with the capacity of generating more than one beam at the same time, which can be treated independently.

In a preferred way, transfer of the laser radiation takes place within pressurized pipes to prevent contamination by external agents. In the case where optical transmission units are present like the ones designated by 2 (with an angle of deflection of, for instance, 90°), these are preferably reflection systems, polarized and cooled with a cooling system to guarantee the thermal stability of the system as a whole, typically in the range of temperatures comprised between 10° C. and 30° C. Before entry into the deflection systems 3, on the path of the laser radiation there can be interposed auxiliary components, such as corrective lenses and/or filters in order to attenuate the optical defects of the aforesaid systems.

Via the deflection units 3 the laser beam or beams is/are moved, transmitted and focused on the work area or treatment window, which comprises and includes a portion or the whole of the article or articles and/or raw materials to be treated.

As has already been said, the deflection units or scanners 3, and the laser generator 1 are commercially available components, chosen so as to meet the specific requirements of the treatment (type of treatment t be carried out, type of raw materials to be treated, etc.).

The experiments conducted by the present applicant prove that, all other parameters being equal (e.g., type and size of the incoming beam arriving from the generator), the diameter of the laser spot at output projected on the working surface, i.e., on the articles A, assumes particular importance.

The diameter of the spot is usually a function of the physical quantities mentioned previously whilst the scanner 3, or deflection unit, is chosen with reference to the speed of the raw material or of the flow of material to be treated and according to the dimensions of the product that is to be treated.

Also for the reasons already explained previously, with reference to the wavelength of the radiation produced by the source 1, i.e., the physical and chemical constitutional characteristics of the raw materials and/or products treated, which are very sensitive to the infusion of energy, it is important to make sure that the energy of the laser treatment is conferred/transferred in an adequately balanced way.

This result can be achieved thanks to the hardware designated by 4 in FIG. 1 and to its action of real-time control of the process variables, such as the power of the laser beam, the instantaneous speed of the laser spot and the size of the laser spot itself.

Speed and power are modulated point by point along the entire profile traced, for example with a frequency of between 20 ns and 50 μs according to the feedbacks of flow speed, position and phase of the article provided by the encoder 5 and by the sensor 6, mechanically connected to the master unit 8 of the process.

For a better understanding of the importance assumed in the context of the solution described herein by the definition of the characteristics of speed and power, as well as size of the laser spot, it is useful to refer to the processes of welding and/or cutting normally carried out on sheet metal.

When two sheets of metal are welded together using conventional techniques, for example with the covered-arc system, the electric arc melts the two sheets of metal and the material of the electrode. During the step of heating and cooling of the weld pool, the areas adjacent to the weld bead are altered thermally, with enlargement of the crystal grain that leads as a consequence to a brittle behaviour of the material. It may in fact be found that, in these cases, the welds do not fail on the bead itself, but in the proximity of the weld, namely in the so-called heat-affected zone (HAZ).

All other parameters being equal, the width of the heat-affected zone is inversely proportional to the welding speed, and the welding speed is in turn linked in an indirectly proportional way to the size of the weld pool, i.e., the larger the weld pool, the lower the welding speed and the larger the heat-affected zone. Welds performed on the sheets of metal using laser technology are faster, have extremely small weld beads and consequently small heat-affected zones.

Likewise, the spot on polymeric materials, such as the materials forming sanitary products are for the most part, should virtually be as small as possible in so far as the aim is, also in this case, to reduce the HAZ, which usually corresponds to a hardened and enlarged edge.

As has already been said previously, the transfer of the beam between the generator 1 and deflection unit 3 occurs within pipes rendered opaque and pressurized to prevent any contamination from outside and at the same time protect operators from any radiation and/or accidental burns.

Any change of direction of the beam occurs using reflection systems (such as surface-lapped and cooled copper mirrors), one or more in number for each laser beam, according to the positioning of the generator with respect to the deflection units 3.

As has been seen, the raw materials and/or the products treated in the framework of the solution described herein, are very sensitive to the infusion of energy, in so far as they are prevalently made up of plastic materials, either synthetic or otherwise, such as, for example, PE, PP, binding resins, cellulose, etc. Very frequently these are extremely thin films of variable thickness and in any case comprised between 10 μm and 1000 μm.

The thickness of the fabrics that are treated is, normally, the result of the process of coupling together of a number of materials. In this case, the thickness of the finished sheet can be of the order of millimetres.

In the case of cutting, the quality of the edge risks undergoing structural deterioration (melting, burns, hardening, etc.) and is linked to the width of the profile treated and hence to the dimensions of the spot performing the treatment, which tends to reduce the diameter to the minimum.

Typically—with preferential, but not imperative reference to the values of wavelength considered previously—said diameter is comprised between 50 μm and 2000 μm, according to the process that it is intended to carry out, whether cutting or welding.

Typically, these are values between 50 μm and 800 μm for a cutting treatment, with preferred values between 100 μm and 300 μm.

For welding treatments wider ranges can be used, from 100 µm to 2000 µm, and typically between 100 µm and 1000 µm, compatibly with the requirements expressed in the design of the product.

Shown in FIGS. 3 to 6 are the profiles of irradiation, with the pattern of the relative energy distribution for the different modes of source that can be used, 00 mode, D mode, or Q mode.

Figure 3:
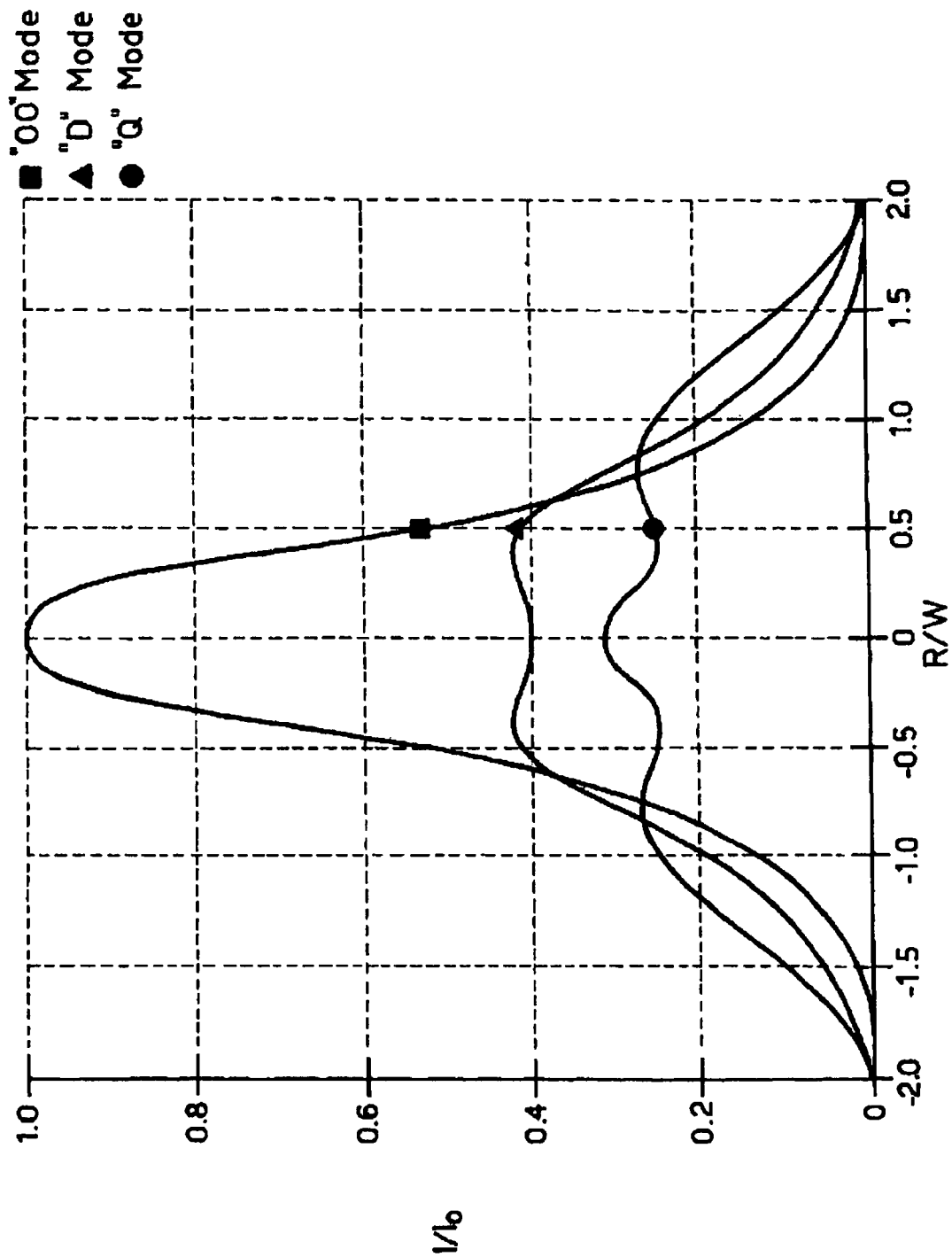
FIGS. 3 to 6 illustrate preferential characteristics of laser sources that can be used in the field of the solution described herein.

In particular, FIG. 3 illustrates, for the three modes in question, the typical pattern of the intensity of emission $I/I_o$ normalized with respect to the reference value $I_o=2P/3$, $141W^2$ where P is the total power and W is the radius of the beam for the mode "00" multiplied by the factor $(1/e^2)$ The scale of the abscissa of FIG. 3 represents the radial co-ordinate R normalized with respect to the factor W.

Figure 6:
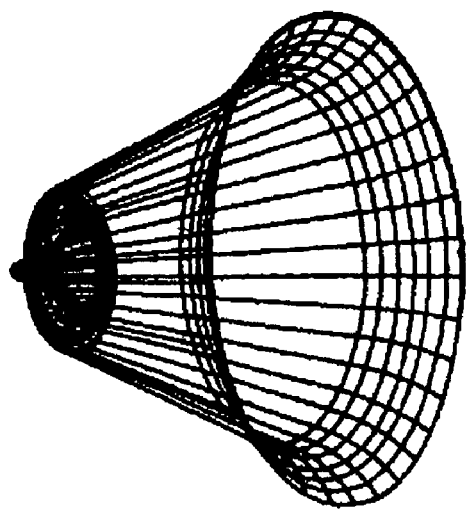
Figure 5:
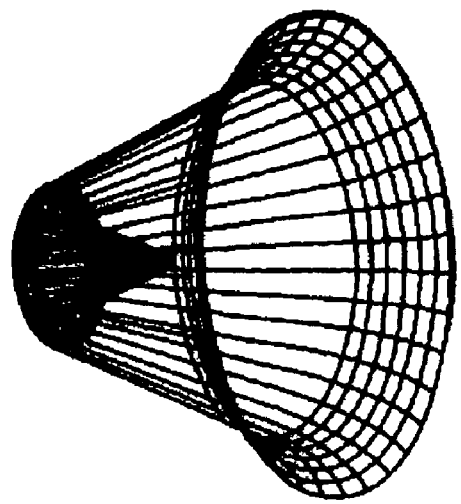
Figure 4:
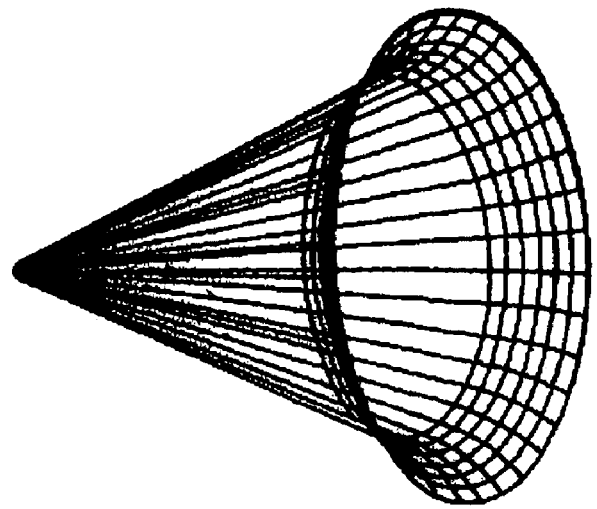

FIGS. 4 to 6 are three-dimensional representations of the three diagrams of FIG. 3.

As already mentioned previously, given the specific Gaussian profile, for the cutting operation the use of the 00 mode is preferred in so far as it has a high concentration of energy in the central area of the curve.

The other two beam modes, Q mode and D mode, on account of their shape, which has a very wide energy front, are preferred for the welding operations.

In any case, it appears preferable to use specific optics under the deflection units 3, which are able to reduce and/or eliminate the defects of perimetral ovalization of the beam, due to errors of parallax and/or spherical aberration and/or quality of the raw materials of the lens. The preferred types of these optics are: SE (individual lens) for reduction of deformation by 50%, DE (double lens) to bring the limit of error to 30%, and TCE (triple lens) to cause the errors to tend to 0%.

As mentioned previously, the values of power and instantaneous speed of "tracing" of the laser beam on the articles A are modulated, controlled and phased through the module 4. Said module, as has already been said, is able to interact in real time on the process itself so as to control the variables involved, instant by instant, along the entire profile traced, with the capacity of reacting in the pre-determined times during programming of the device.

The treatment of the specific materials of the sanitary products must be carried out so as not to alter the quality of the materials themselves. The solution described herein enables this result to be achieved in so far as it enables precise regulation of the main variables that are involved in the process, such as:

the power P of the laser beam;

the instantaneous relative speed V of the laser beam with respect to the sheet of material to be processed; and the instantaneous diameter D of the treatment spot.

For example, the experiments conducted by the present applicant show that it is possible to obtain a cut of good quality ensuring that the following relation is verified:

$$\frac{\text{Power}}{\text{Speed of spot}} \geq K$$

where we have:

$$\frac{P}{D \times V} \geq K$$

the value K has the dimensions:

$$\frac{w}{m \cdot \frac{m}{s}} = \frac{w \cdot s}{m^2} = \frac{J}{m^2}$$

In particular, good cutting results are obtained with values of K of between 25 and 1000 kJ/m², with preferential values for combinations of two materials, one polypropylene-based and one polyethylene-based, of between 100 and 300 kJ/m².

It should be noted that all three physical quantities that are involved in the definition of the value K are variables, in particular speed and power, are dependent variables, whilst the diameter of the spot is an independent variable.

In other words, the diameter of the spot has the minimum value when the beam is positioned at the centre of the work window of the scanner 3, whilst it increases in size when the beam shifts towards the edges of the work window. This increase in size of the spot depends upon the fact that, when the beam works in the central area, it is practically a circumference, whereas, when it works in the periphery of the work area, it is transformed into an ellipse with the minor diameter equal to the diameter of the circumference of the spot. The D that must be taken into consideration in the formula for determination of K, in this latter case, is the major diameter of the ellipse.

It is evident that the amplitude of the work area depends upon the shape of the product that it is desired to obtain, and consequently it cannot be varied (independent variable).

To maintain the value K always higher than the minimum value for which there is an acceptable cutting quality, the two dependent variables, power and speed, are modulated together or individually.

In order to be able to govern speed and power, the module 4 is used, which is typically configured in order to:

modulate the power of the laser beam according to the speed of the flow of articles A along the axis z, detected by the encoder 5, which is connected mechanically in the ratio of 1 turn to 1 article to the master unit of the process; the resolution of the encoder depends upon the speed of the process and upon the complexity of the profile treated and is typically comprised between 1000 and 10,000 counts per turn;

phase the clock for start and end of treatment of the profile defined on the flow along the axis z; this is obtained thanks to the master sensor (encoder) 8, positioned so as to act along the axis z;

modulate in real time the intensity of the vectors of the instantaneous speed of tracing, as a function of the position on the profile of tracing of the spot and as a function of the speed of the flow of the articles A in the transients of ramp of acceleration and deceleration of the device;

modulate, instant by instant, in the course of tracing of the profile, the intensity and direction of the transverse component of the velocity vector of the spot, defined along the axis x normal to the direction z of advance of the articles, so as to guarantee a resultant instantaneous tangential velocity that is suitable for guaranteeing the minimum desired value of K; the aforesaid modulation of velocity generates a further advantage in so far as it brings about a reduction of the work window in the direction z, with consequent reduction of the effects of ovalization of the beam due to the errors of parallax and/or spherical aberration of the focusing optics in the deflection systems 3; and modulate in real time the intensity of the power of the spot for cutting/welding, as a function of the position on the profile of tracing of the spot and as a function of the speed of the flow of the articles A, so as to guarantee an instantaneous power suitable for producing the minimum value of K desired both during the operation in steady-state conditions and during the transients of ramp of acceleration and deceleration of the device.

The modulation of power is possible in so far as the control unit 4 possesses a 0-10-V analog output module, which enables driving of the laser source in so far as the card for controlling the power of the generator accepts such an analog driving signal.

Of course, without prejudice to the principle of the invention, the details of construction and the embodiments may vary widely with respect to what is described and illustrated herein purely by way of non-limiting example, without thereby departing from the scope of the present invention as defined in the annexed claims.

The invention claimed is:

1. A method of subjecting articles chosen between sanitary products and components of said products to laser cutting treatment along a pre-set path, the laser treatment comprising:
   applying to said articles a laser spot and producing a relative movement of scanning between said laser spot and said articles along said pre-set path, the laser spot having a diameter of between 50 µm and 800 µm, said laser spot having a wavelength between 9.6 µm and 11.0 µm; and
   regulating in real time during the scanning jointly the power of said laser spot, the instantaneous relative speed of said laser spot with respect to the article treated and the instantaneous diameter of the laser spot so that the following relation is satisfied:

$$\frac{P}{D \times V} \geq K$$

where

P is the power of said laser spot,

V is the instantaneous relative speed of said laser spot with respect to the article treated, D is the instantaneous diameter of the laser spot, and K is a threshold value chosen between 100 kJ/m$^2$ and 300 kJ/m$^2$.

2. The method according to claim 1, wherein said laser spot has a wavelength chosen between 9.6 µm and 10.6 µm.

3. The method according to claim 1 wherein said laser spot is with beam mode OO MODE.

4. The method according to claim 1 further comprising the steps of:
   generating said laser spot with a non-parallel-laser-beam source, and
   regulating the diameter of the laser spot by varying the optical distance between said source and said articles.

5. The method according to claim 4 further comprising the steps of:
   applying said laser spot to said articles via at least one deflection unit, and
   regulating the diameter of the laser spot by varying the distance between said source and said at least one deflection unit.

6. The method according to claim 1 further comprising the steps of:
   generating said laser spot with a laser-beam source, and
   conveying said laser beam from said source towards said articles through pressurized pipes.

7. The method according to claim 1 further comprising the steps of:
   generating said laser spot with a laser-beam source, and
   conveying said laser beam from said source towards said articles through at least one reflection system.

8. The method according to claim 7 further comprising cooling said reflection system.

9. The method according to claim 1 further comprising regulating the power associated to said laser spot in the range between 100 W and 1000 W.

10. The method according to claim 1 further comprising maintaining substantially constant the instantaneous speed of scanning of said articles by the laser spot.

11. The method according to claim 1 further comprising producing said relative movement of scanning as the resultant between a movement of advance of said articles in a direction (z) and a movement of deflection of said laser spot, said movement of deflection having at least one component in a transverse direction (x) with respect to the direction (z) of said movement of advance of the articles.

12. The method according to claim 1 further comprising maintaining active or deactivating selectively said laser spot according to the position reached in said scanning movement.

13. The method according to claim 1 further comprising counteracting the defects of perimetral ovalization of said laser spot via specific optics.

14. The method according to claim 1 further comprising supporting said articles by means of at least one of belt and drum elements.

15. The method according to claim 1 further comprising supporting said articles via controlled-temperature elements.

16. The method according to claim 1 further comprising supporting said articles via at least one element coated with a layer of anti-adherent material, such as neutral silicone.

17. The method according to claim 1, wherein the laser spot has a diameter between 100 µm and 300 µm.

18. The method according to claim 1, wherein the laser spot has a wavelength of about 10.2 µm.

19. A device for subjecting articles chosen between sanitary products and components of said products to laser cutting treatment along a pre-set path, the device comprising;
   a laser-beam source configured for applying to said articles a laser spot with a diameter of between 50 µm and 800 µm, said laser spot having a wavelength between 9.6 µm and 11.0 µm,
   at least one system of movement for producing a scanning movement between said laser spot and said articles; and
   a control unit configured for regulating jointly the power of said laser spot, the instantaneous relative speed of said laser spot with respect to the article treated, and the instantaneous diameter of the treatment laser spot so that the following relation is satisfied:

$$\frac{P}{D \times V} \geq K$$

where

P is the power of said laser spot,

V is the instantaneous relative speed of said laser spot with respect to the article treated, D is the instantaneous diameter of the laser spot, and K is a threshold value chosen between 100 kJ/m$^2$ and 300 kJ/m$^2$.

20. The device according to claim 19, wherein said laser spot has a wavelength chosen between 9.6 μm and 10.6 μm.

21. The device according to claim 19, wherein said laser spot is with beam mode chosen between OO MODE.

22. The device according to claim 19 wherein said source is a non-parallel laser beam source and the optical distance between said source and said articles is variable for regulating the diameter of said laser spot.

23. The device according to claim 22 further comprising at least one deflection unit for applying said laser spot to said articles and in that the distance between said source and said at least one deflection unit is variable for regulating the diameter of said laser spot.

24. The device according to claim 19 further comprising pressurized pipes to convey said laser beam from said source towards said articles.

25. The device according to claim 19 further comprising at least one reflection system to convey said laser beam from said source towards said articles.

26. The device according to claim 25, wherein said reflection system is refrigerated and/or polarized.

27. The device according to claim 19, wherein the power associated to said laser spot is comprised in the range between 100 W and 1000 W.

28. The device according to claim 19 further comprising a control unit configured for regulating and/or modulating the power associated to said laser spot as a function of at least one between the speed of the articles and the instantaneous position of the spot on the line of scanning of said articles by the spot itself.

29. The device according to claim 19 further comprising a control unit configured for maintaining substantially constant the speed of the articles and the instantaneous position of the spot along the pre-defined perimeter of marking, and hence the instantaneous intensity of the resulting vectors.

30. The device according to claim 19, wherein said system of movement comprises:
   a conveyor, for producing a movement of advance of said articles in one direction (z); and
   at least one deflection unit for regulating or producing a movement of deflection of said laser spot with at least one component in a transverse direction (x) with respect to the direction (z) of said movement of advance of the articles.

31. The device according to claim 19 further comprising a control unit configured for activating and/or deactivating selectively said laser spot according to the position reached in said scanning movement.

32. The device according to claim 19 further comprising optical units for counteracting the defects of perimetral ovalization of said laser spot.

33. The device according to claim 32, wherein said optical units are chosen between single lens, double lens, and triple lens optics.

34. The device according to claim 19 further comprising at least one of belt and drum elements for supporting said articles.

35. The device according to claim 19 further comprising controlled-temperature elements for supporting said articles.

36. The device according to claim 19 further comprising at least one element coated with a layer of anti-adherent material, such as neutral silicone for supporting said articles.

37. The system according to claim 19, wherein the laser spot has a diameter between 100 μm and 300 μm.

38. The system according to claim 19, wherein the laser spot has a wavelength of about 10.2 μm.

* * * * *

UNITED STATES PATENT AND TRADEMARK OFFICE
CERTIFICATE OF CORRECTION

PATENT NO. : 7,528,343 B2 Page 1 of 1
APPLICATION NO. : 11/391955
DATED : May 5, 2009
INVENTOR(S) : Lupinetti et al.

It is certified that error appears in the above-identified patent and that said Letters Patent is hereby corrected as shown below:

In the claims:

Claim 21, Col. 13, Line 4: Delete "spot is with beam mode chosen between OO MODE." and insert -- spot is with beam mode OO MODE. --

Signed and Sealed this

Twenty-eighth Day of July, 2009

JOHN DOLL
*Acting Director of the United States Patent and Trademark Office*